(12) United States Patent
Min

(10) Patent No.: US 10,894,165 B2
(45) Date of Patent: Jan. 19, 2021

(54) FEEDTHROUGH DEVICE

(71) Applicant: Kyou Sik Min, Suwon-si (KR)

(72) Inventor: Kyou Sik Min, Suwon-si (KR)

(73) Assignee: Kyou Sik Min

( * ) Notice: Subject to any disclaimer, the term of this patent is extended or adjusted under 35 U.S.C. 154(b) by 125 days.

(21) Appl. No.: 16/069,654

(22) PCT Filed: Jan. 13, 2017

(86) PCT No.: PCT/KR2017/000480
§ 371 (c)(1),
(2) Date: Jul. 12, 2018

(87) PCT Pub. No.: WO2017/123051
PCT Pub. Date: Jul. 20, 2017

(65) Prior Publication Data
US 2019/0022398 A1    Jan. 24, 2019

(30) Foreign Application Priority Data

Jan. 13, 2016    (KR) .................. 10-2016-0004231

(51) Int. Cl.
*A61N 1/375*    (2006.01)
*A61B 5/00*    (2006.01)
(Continued)

(52) U.S. Cl.
CPC .............. *A61N 1/3754* (2013.01); *A61B 5/00* (2013.01); *A61N 1/362* (2013.01); *H01G 2/106* (2013.01); *H05K 1/0306* (2013.01)

(58) Field of Classification Search
CPC ........ A61B 5/00; A61N 1/362; A61N 1/3754; H01G 2/106; H05K 1/0306
See application file for complete search history.

(56) References Cited

U.S. PATENT DOCUMENTS

| 5,333,095 A | * | 7/1994 | Stevenson | ............ | A61N 1/3754 29/25.42 |
| 6,351,369 B1 | | 2/2002 | Kuroda et al. | | |

(Continued)

FOREIGN PATENT DOCUMENTS

| EP | 0 623 363 A2 | 11/1994 |
| EP | 2 667 938 A1 | 12/2013 |

(Continued)

OTHER PUBLICATIONS

International Search Report and Written Opinion issued in PCT/KR2017/000480, dated Apr. 21, 2017; ISA/KR.

(Continued)

*Primary Examiner* — Jonathan T Kuo
(74) *Attorney, Agent, or Firm* — Harness, Dickey & Pierce, P.L.C.

(57) ABSTRACT

The present invention provides a feedthrough device including: a feedthrough substrate made of an insulator and having a first surface and a second surface; at least one first feedthrough conductor having a terminal exposed to the first surface of the feedthrough substrate and a body connected to the terminal and not exposed to the outside of the feedthrough substrate; and at least one second feedthrough conductor having a terminal exposed to the second surface of the feedthrough substrate and a body connected to the terminal and not exposed to the outside of the feedthrough substrate, and corresponding to the first feedthrough conductor in a one-to-one manner to be paired therewith, wherein a body of each first feedthrough conductor and a body of each second feedthrough conductor corresponding thereto are arranged to be capacitively coupled with each other.

14 Claims, 14 Drawing Sheets

(51) Int. Cl.
*A61N 1/362* (2006.01)
*H01G 2/10* (2006.01)
*H05K 1/03* (2006.01)

(56) References Cited

U.S. PATENT DOCUMENTS

| | | |
|---|---|---|
| 6,414,835 B1 | 7/2002 | Wolf et al. |
| 7,481,672 B2 | 1/2009 | Edvardsson |
| 7,797,048 B2 | 9/2010 | Stevenson et al. |
| 8,577,453 B1 | 11/2013 | Stevenson et al. |
| 9,493,261 B2 * | 11/2016 | Taff ................ A61B 50/00 |
| 2007/0020998 A1 | 1/2007 | Edvardsson |
| 2010/0100164 A1 * | 4/2010 | Johnson ............ H01F 27/027 |
| | | 607/116 |
| 2013/0184797 A1 | 7/2013 | Tang et al. |
| 2015/0142073 A1 * | 5/2015 | Taff ................ A61N 1/362 |
| | | 607/36 |

FOREIGN PATENT DOCUMENTS

| | | |
|---|---|---|
| JP | 2009501933 A | 1/2009 |
| KR | 100364009 B1 | 12/2002 |

OTHER PUBLICATIONS

Partial Supplementary European Search Report for Application No. EP 17738680 dated Jul. 17, 2019 (10 pages).

European Search Report regarding EP 17738680.2, dated Dec. 17, 2019.

Y. Kuo et al., Using simulation and multi-criteria methods to provide robust solutions to dispatching problems in a flow shop with multiple processors, Mathematics and Computers in Simulation, Elsevier, Amsterdam, NL, vol. 78, No. 1, Jun. 1, 2008 (Jun. 1, 2008), pp. 40-56, XP022615480.

* cited by examiner

Fig. 15
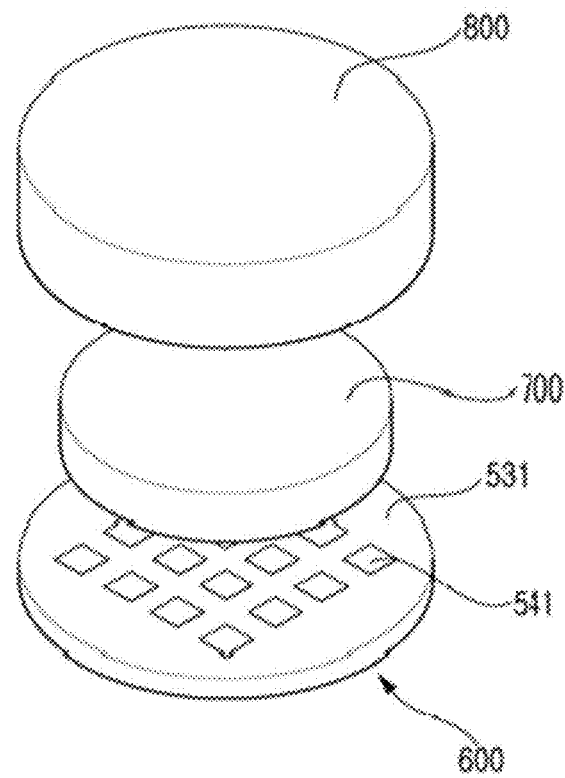
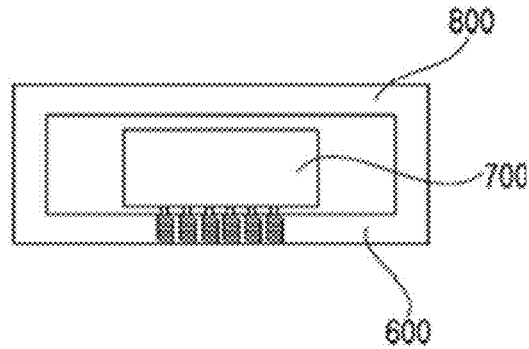

FEEDTHROUGH DEVICE

CROSS-REFERENCE TO RELATED APPLICATION

This Application is a Section 371 National Stage Application of International Application No. PCT/KR2017/000480, filed Jan. 13, 2017. This application claims the benefit of priority from Korean Application No. 10-2016-0004231, filed Jan. 13, 2016. The contents of both applications are hereby incorporated by reference in their entirety.

TECHNICAL FIELD

The present invention relates to a feedthrough device and, more particularly, to a feedthrough device for an implantable medical device.

BACKGROUND ART

Implantable medical devices such as implantable stimulator, implantable sensor, implantable cardioverter-defibrillator, neuroprosthetics, and neuromodulation device require secure sealing since the devices operate while implanted in vivo. If a sealing state of a device is bad, body fluid may leak into electronic circuit boards present inside the device, leading to failure, malfunction, reduced service life, etc. of the device.

Of particular concern with device sealing is the sealing associated with a feedthrough device provided with the device. The feedthrough device is also referred to as a feedthrough assembly that is provided in a housing of the device to provide an electrical connection path between an electronic circuit board within the device and components such as leads, electrodes, sensors, etc., the components being present inside the human body and outside the device.

FIG. 1 is an exploded perspective view roughly showing an implantable medical device applied with a feedthrough device of the related art. As shown above, the implantable medical device 1 of the related art is provided with a housing 2 made of titanium or titanium alloy (FIG. 1 shows a configuration thereof including an upper housing component 2a, a middle housing component 2b, and a lower housing component 2c, from top to bottom), an electronic circuit board 3 mounted inside the housing 2, and a feedthrough device 4 mounted to a coupling groove 2d, which is formed through the housing 2, in a inserted manner. For convenience of explanation, the feedthrough device 4 is shown enlarged as compared to the housing 2.

The feedthrough device 4 includes a feedthrough substrate 5 made of an insulator such as ceramic, etc. and multiple feedthrough conductors 6 fixed to the feedthrough substrate 5 in a penetrating manner.

In the implantable medical device 1 in the related art having the above structure, in order to prevent body fluid from leaking into the electronic circuit board 3 through the feedthrough device 4, the housing 2 made of titanium or titanium alloy and the feedthrough substrate 5 are joined together by brazing (process in which a filler metal is applied to different types material of junctions and heated to high temperature about 1000° C. for joining). In addition, boundary portions between the feedthrough substrate 2 made of an insulator such as ceramic, etc. and the feedthrough conductors 6 made of metal are also joined together by brazing to improve the sealing. That is, as shown in FIG. 2, which shows a photograph of a sealing structure of the boundary portions between the feedthrough substrate 5 and the feedthrough conductors 6 according to the related art, the boundary portions between the feedthrough substrate 5 and the feedthrough conductors 6 are joined by brazing such that ring-shaped brazing joints 7 are formed.

Although there are attempts to improve the sealing of implantable medical devices having a feedthrough device by such complicated and demanding processes, most defects or failures of implantable medical devices are caused by leakage of body fluid through a feedthrough device, whereby it is difficult to accept that the implantable medical devices of the related art are reliable and successful with respect to sealing of the devices.

Accordingly, there is still demand from the related industry for a technique that can easily and reliably prevent leakage of body fluid through a feedthrough device.

DISCLOSURE

Technical Problem

Accordingly, the present invention has been made keeping in mind the above problems occurring in the related art, and an object of the present invention is to provide a feedthrough device, the device capable of easily preventing leakage through the device without need for complicated and cumbersome processes such as brazing.

In addition, another object of the present invention is to provide a feedthrough device in which the structure thereof is transformed such that the cause of leakage is fundamentally eliminated, thereby capable of ensuring the prevention of leakage through the feedthrough device.

Technical Solution

In order to accomplish the above and other objects, a feedthrough device includes: a feedthrough substrate made of an insulator and having a first surface and a second surface; at least one first feedthrough conductor having a terminal exposed to the first surface of the feedthrough substrate and a body connected to the terminal and not exposed to the outside of the feedthrough substrate; and at least one second feedthrough conductor having a terminal exposed to the second surface of the feedthrough substrate and a body connected to the terminal and not exposed to the outside of the feedthrough substrate, and corresponding to the first feedthrough conductor in a one-to-one manner to be paired therewith, wherein a body of each first feedthrough conductor and a body of each second feedthrough conductor corresponding thereto are arranged to be capacitively coupled with each other.

In order to accomplish the above and other objects, an implantable medical device includes: a housing and a feedthrough device provided inside the housing, wherein the feedthrough device includes: a feedthrough substrate made of an insulator and having a first surface and a second surface; at least one first feedthrough conductor having a terminal exposed to the first surface of the feedthrough substrate and a body connected to the terminal and not exposed to the outside of the feedthrough substrate; and at least one second feedthrough conductor having a terminal exposed to the second surface of the feedthrough substrate and a body connected to the terminal and not exposed to the outside of the feedthrough substrate, and corresponding to the first feedthrough conductor in a one-to-one manner to be paired therewith, wherein a body of each first feedthrough conductor and a body of each second feedthrough conductor corresponding thereto are arranged to be capacitively coupled with each other.

In order to accomplish the above and other objects, a method of manufacturing a feedthrough device, the method includes: forming a molded body, which includes capacitive stacks and a third film interposed between adjacent capacitive stacks and is configured in which a first, a second, and the third films are bonded together, the capacitive stacks including a structure in which a plurality of first films each provided with one or more first conductive plates spaced apart from each other and a plurality of second films each provided with one or more second conductive plates spaced apart from each other are alternately stacked in a manner that the first conductive plate and the second conductive plate are alternated in order to configure a superimposed portion in which each of the first conductive plate and the second conductive plate superimposes on an orthographic projection of conductive plates adjacent in a vertical direction and a non-superimposed portion which does not superimpose on the orthographic projections; cutting the molded body along a stacked direction such that at least one cut body is configured in which an end portion of the non-superimposed portion of the first conductive plate is exposed to a first surface and an end portion of the non-superimposed portion of the second conductive plate a second surface which is opposite to the first surface; forming a terminal integration body in which multiple first terminals connecting end portions of the non-superimposed portion of the first conductive plate belonging to first stacked body constituting the cut body are formed on the first surface, and multiple second terminals connecting the end portions of the non-superimposed portion of the second conductive plate belonging to each first stacked body are formed on the second surface; and cutting the terminal integration body perpendicular to the stacked direction in a manner that the multiple first terminals and the corresponding multiple second terminals are included.

Advantageous Effects

In a feedthrough device according to the present invention, a feedthrough conductor does not penetrate a feedthrough substrate whereby leakage through the feedthrough device can be prevented simply without need for complicated and cumbersome processes such as brazing for sealing between the feedthrough substrate and the feedthrough conductor.

In addition, the structure of the feedthrough device is transformed in which the feedthrough conductor does not penetrate the feedthrough substrate such that the cause of leakage is fundamentally eliminated, whereby the prevention of leakage through the feedthrough device can be ensured.

Furthermore, in the feedthrough device according to the present invention, a pair of feedthrough conductors are capacitively coupled such that direct current can be blocked by the feedthrough device whereby it is advantageous in terms of cost since a separate DC capacitor is not necessary to be provided on an electronic circuit board, and thus the electronic circuit board can be simplified, and efficient circuit integration can be achieved.

DESCRIPTION OF DRAWINGS

FIG. 15 is an exemplary diagram showing a feedthrough device manufactured by the method shown in FIGS. 10 to 14.

MODE FOR INVENTION

Figure 1:
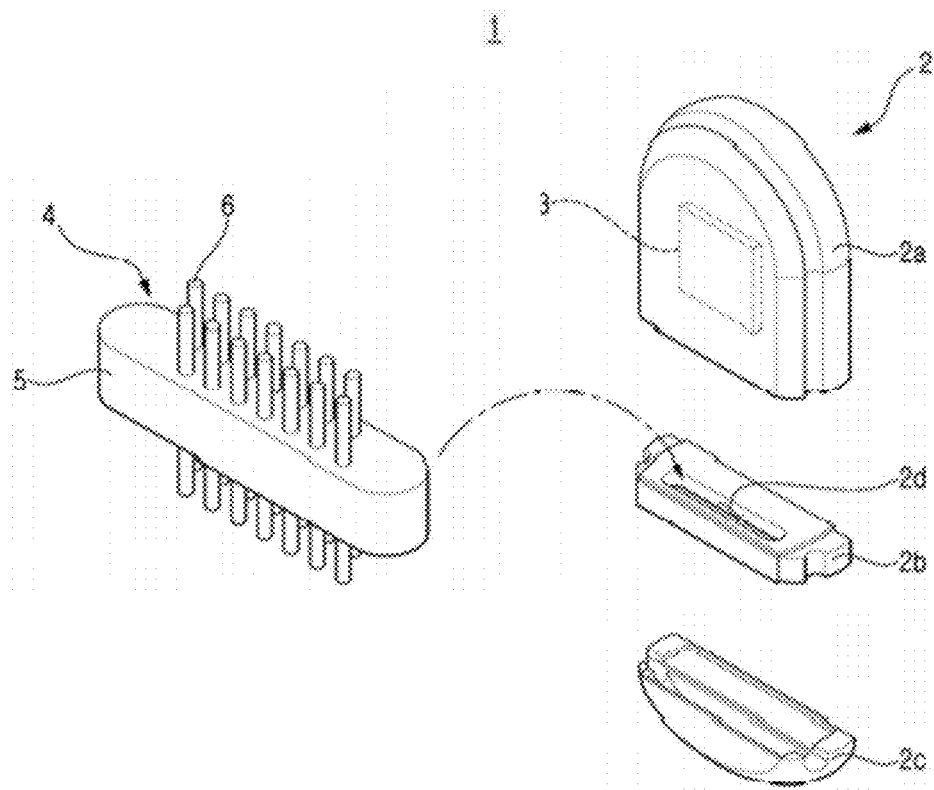
FIG. 1 is an exploded perspective view roughly showing an implantable medical device applied with a feedthrough device of the related art.

The above and other objects, features, advantages, and methods for achieving them of the present invention will be more clearly understood from the following detailed embodiments when taken in conjunction with the accompanying drawings. The embodiments described hereinbelow are provided for fully conveying the scope and spirit of the invention to those skilled in the art, so it should be understood that the embodiments may be changed to a variety of embodiments and the scope and spirit of the invention are not limited to the embodiments described hereinbelow. The scope of the present invention is defined only by the accompanying claims and their equivalents if appropriate. It should be understood that the terminology used herein is for the purpose of describing particular embodiments only and is not intended to limit the meaning of elements or to limit the scope and spirit of the invention. An element expressed in a singular form in this specification may be plural elements unless it is necessarily singular in the context.

Wherever possible, the same reference numerals will be used throughout the drawings and the description to refer to the same or like elements or parts. In the following description, it is to be noted that, when the functions of conventional elements and the detailed description of elements related with the present invention may make the gist of the present invention unclear, a detailed description of those elements will be omitted.

Figure 3:
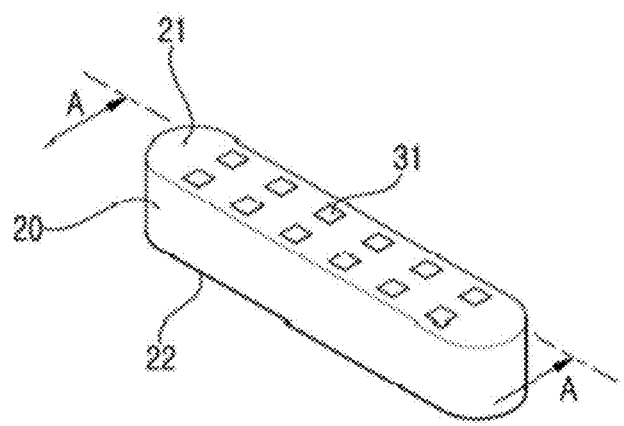
FIG. 3 is a perspective view showing a feedthrough device according to an embodiment of the present invention.
Figure 4:
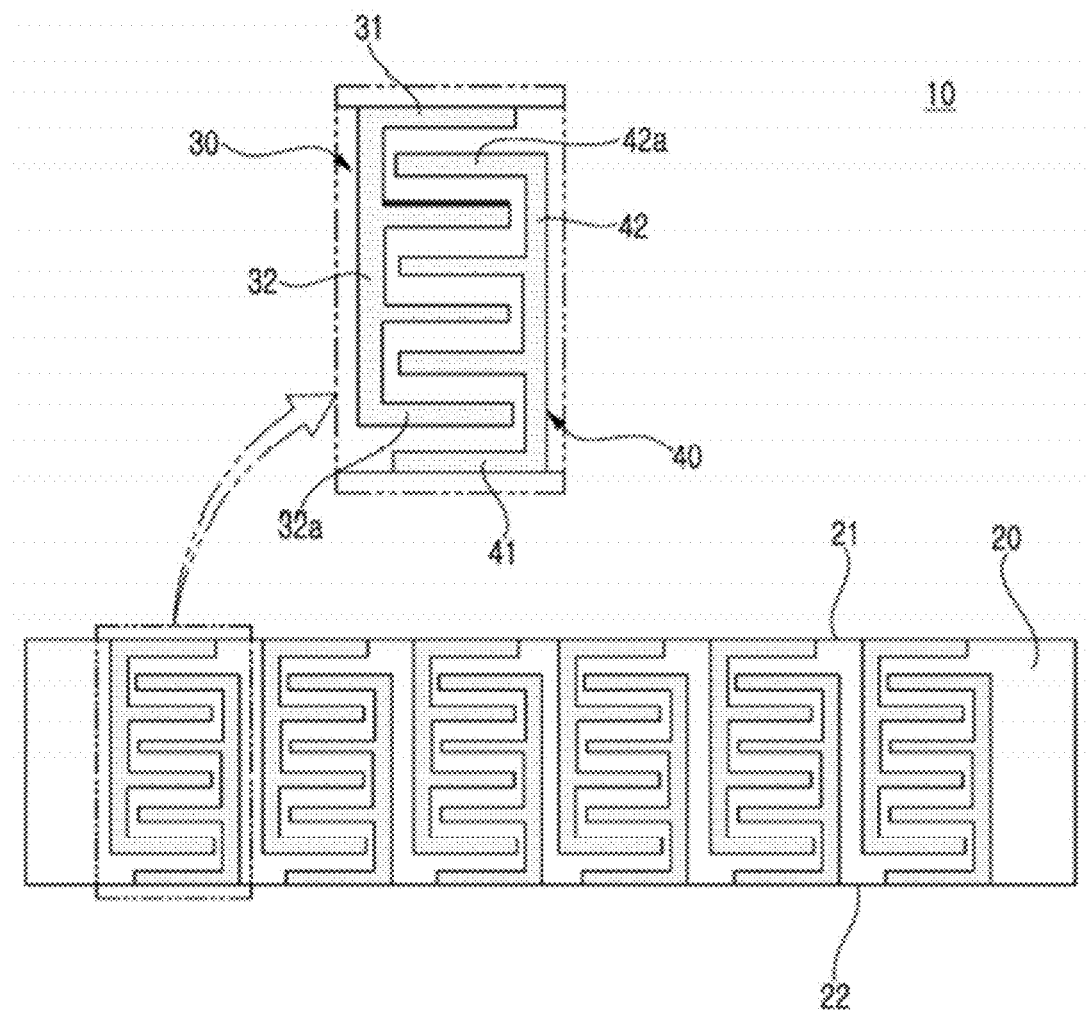
FIG. 4 is a cross-sectional view taken along line A-A of FIG. 3.

FIG. 3 is a perspective view showing a feedthrough device according to an embodiment of the present invention; and FIG. 4 is a cross-sectional view taken along line A-A of FIG. 3.

Referring to FIGS. 3 and 4, a feedthrough device 10 according to the embodiment of the present invention includes a feedthrough substrate 20, at least one first feedthrough conductor 30, and at least one second feedthrough conductor 40. The feedthrough substrate has a first surface 21 and a second surface 22, which are an upper surface and a lower surface thereof respectively. The first feedthrough conductor 30 is provided with a terminal 31 and a body 32, the terminal being exposed to the first surface 21 and the body 32 being disposed inside the feedthrough substrate 20 to not be exposed to outside the feedthrough substrate 20. The second feedthrough conductor 40 is also provided with a terminal 41 and a body 42, the terminal 41 being exposed to the second surface 22 and the body 42 being disposed inside the feedthrough substrate 20 to not be exposed to outside the feedthrough substrate 20. The first feedthrough conductor 30 and the second feedthrough conductor 40 correspond to each other in a one-to-one manner to be paired therewith, the body 32 of the first feedthrough conductor and the body 42 of the second feedthrough conductor corresponding thereto are arranged to be capacitively coupled with each other.

As shown in FIG. 4, in order to enhance the capacitive coupling, a body 32 of each first feedthrough conductor 30 may be provided with at least one branch 32a, and a body 42 of each second feedthrough conductor 40 which corresponds to the first feedthrough conductor 30 may be provided with at least one branch 42a. Accordingly, the first feedthrough conductor 30 and the second feedthrough conductor 40 corresponding thereto are disposed such that the branches 32a and 42a are arranged in an alternate manner.

The alternate branches 32a and 42a are not necessarily parallel, but the branch 32a of the first feedthrough conductor 30 and the alternately arranged branch 42a of the second feedthrough conductor 40 corresponding thereto may be substantially parallel in order to further enhance the capacitive coupling.

As described, the first surface 21 and the second surface 22 of the feedthrough substrate 20 may be substantially parallel. At the same time, the branch 32a of the first feedthrough conductor 30 and the branch 42a of the second feedthrough conductor 40 may be substantially parallel to the first surface 21 and the second surface 22 of the feedthrough substrate 20.

Figure 5:
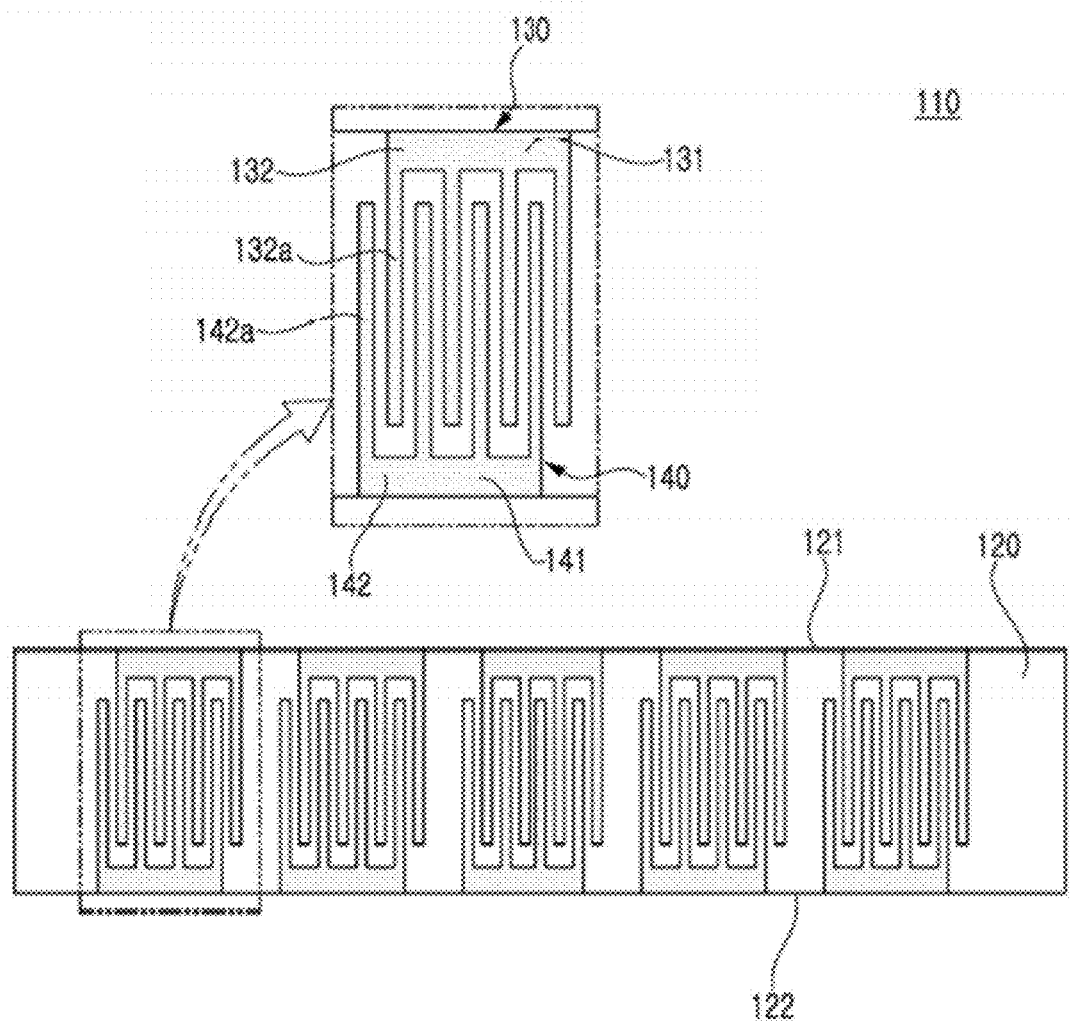
FIG. 5 is a cross-sectional view showing a feedthrough device according to another embodiment of the present invention.

FIG. 5 is a cross-sectional view showing a feedthrough device according to another embodiment of the present invention.

Referring to FIG. 5, a feedthrough device 110 according to the embodiment of the present invention includes a feedthrough substrate 120, at least one first feedthrough conductor 130, and at least one second feedthrough conductor 140, wherein a body 132 of each first feedthrough conductor 130 is provided with at least one branch 132a, and a body 142 of each second feedthrough conductor 140 which corresponds to the first feedthrough conductor 130 is provided with at least one branch 142a. Reference numerals 131 and 141 represent terminals of the conductors 130 and 140, respectively. The first feedthrough conductor 130 and the second feedthrough conductor 140 corresponding thereto are disposed such that the branches 132a and 142a are arranged in an alternate manner. In addition, a first surface 121 and a second surface 122 of the feedthrough substrate 120 are substantially parallel, and the branch 132a of the first feedthrough conductor 130 and the branch 142a of the second feedthrough conductor are substantially perpendicular to the first surface 121 and the second surface 122 of the feedthrough substrate 120.

FIG. 4 shows the branches 32a and 42a are substantially parallel to the first surface 21 and the second surfaces 22 of the feedthrough substrate 20, and FIG. 5 shows the branches 132a and 142a are substantially perpendicular to the first surface 121 and the second surface 122 of the feedthrough substrate 120, but the present invention is not limited thereto. It should be understood that the present invention includes a case where the branches incline at a predetermined angle with respect to the first surfaces 21 and 121 and the second surfaces 22 and 122, and also includes a case where the first surfaces 21 and 121 and the second surfaces 22 and 122 are not parallel to each other.

In the embodiment shown in FIG. 4, the first surface 21 and an upper surface of the terminal 31 of the first feedthrough conductor 30 have the same height, and the second surface 22 and an upper surface of the terminal 41 of the second feedthrough conductor 40 have the same height, and the embodiment shown in FIG. 5 is also the same. However, the present invention is not limited thereto, and although it is not shown in detail, it should be understood that the present invention includes a case where the height of the upper surface of the terminal is lower than the height of the first surface or second surface of the feedthrough substrate in a recessed manner, or conversely, a case where the height of the upper surface of the terminal is higher than the height of the first surface or second surface of the feedthrough substrate in a protruding manner. The protruding height or recessed depth of the terminal may vary depending on a shape of a corresponding terminal electrically connected thereto and/or a coupling method therebetween.

As shown in FIGS. 4 and 5, the bodies 32 of the first feedthrough conductor 30 may be disposed to be spaced apart from each other at an equal interval, and the bodies 132 of the first feedthrough conductor 130 may be disposed to be apart from each other at an equal interval. In addition, the bodies 42 of the second feedthrough conductor 40 paired with the first feedthrough conductor 30 may be disposed to be apart from each other at an equal interval, and the bodies 142 of the second feedthrough conductor 140 paired with the first feedthrough conductor 130 may be disposed to be apart from each other at an equal interval. Such an arrangement means that the pairs of the conductors consisting of the first feedthrough conductors 30 and 130 and the corresponding second feedthrough conductors 40 and 140 have the same intervals from each other and thus have symmetry or uniformity. Having uniformity in the arrangement means that needs to treat different pairs of conductors differently are reduced, which is advantageous for signal transmission and analysis of received signals through a pair of conductors.

In an implantable medical device provided with the above-described feedthrough device, an electric signal generated in an electronic circuit (not shown) in the device is transmitted to the bodies 32 and 132 of the first feedthrough conductors 30 and 130 through the terminals 31 and 131 of the first feedthrough conductors 30 and 130 of the feedthrough devices 10 and 110. Then, the electric signal is transmitted to external leads, electrodes, sensors, etc., which are connected to the terminals 41 and 141 of the second feedthrough conductors 40 and 140, through the bodies 42 and 142 of the second feedthrough conductors 40 and 140, which are capacitively coupled with the bodies 32 and 132 of the first feedthrough conductors 30 and 130 respectively. On the contrary, an electric signal generated in external leads, electrodes, sensors, etc. is transmitted to the bodies 42 and 142 of the second feedthrough conductors 40 and 140 through the terminals 41 and 141 through the second feedthrough conductors 40 and 140 of the feedthrough devices 10 and 110. Then, the electric signal is transmitted to the electronic circuit in the device, which is connected to the terminals 31 and 131 of the first feedthrough conductors 30 and 130, through the bodies 32 and 132 of the first feedthrough conductors 30 and 130 which are capacitively coupled with the bodies 42 and 142 of the second feedthrough conductors 40 and 140. Here, because the signal transmission according to the pairs of the first and second feedthrough conductors (30 and 40, or, 130 and 140) results from capacitive coupling, it is required that a signal transmitted from the inside and the outside of the device to the feedthrough devices 10 and 110 is not to be direct current (DC). This is because it is impossible for DC to pass through the capacitively coupled conductor pair.

It is rather advantageous that it is impossible for DC to pass through the feedthrough devices 10 and 110 in that the feedthrough devices 10 and 110 of the present invention that are used in vivo such as human bodies. Flow of DC into the living body by implantable medical devices is not allowed for safety reasons. Thus, in implantable medical devices of the related art, in order to suppress undesired DC generated in an electronic circuit board (for example, electronic circuit board 3 of FIG. 1) in the implantable medical device from leaking into the body, a separate DC capacitor is generally provided on the electronic circuit board. However, in the feedthrough devices 10 and 110 according to the present invention, the feedthrough conductor pairs (30 and 40, or, 130 and 140) are capacitively coupled such that the DC is possible to be blocked by the feedthrough device, whereby it is advantageous in terms of cost since a separate DC capacitor is not necessary to be provided on an electronic circuit board, and thus the electronic circuit board can be simplified, and efficient circuit integration can be achieved.

Figure 2:
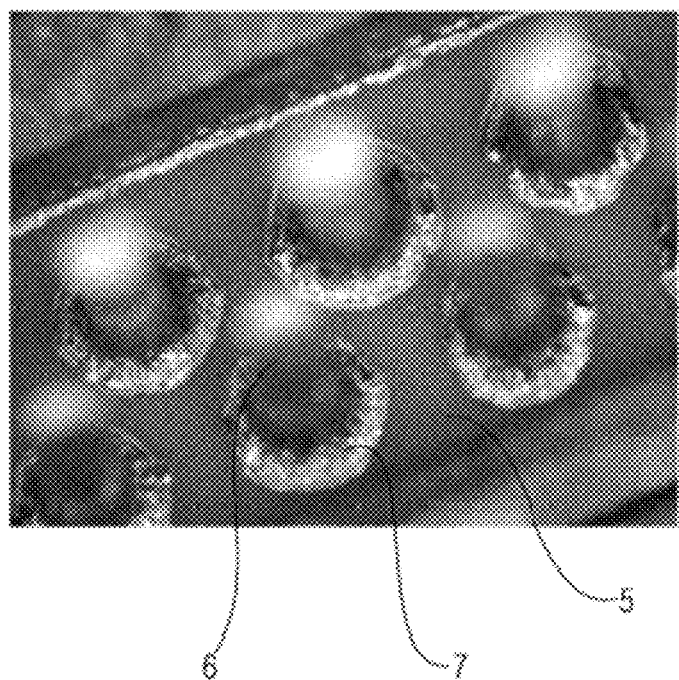
FIG. 2 is a photograph showing a sealing structure of boundary portions between a feedthrough substrate and feedthrough conductors of a feedthrough device according to the related art.

Above all, unlike the related art shown in FIGS. 1 and 2, the feedthrough devices 10 and 110 according to the present invention have no feedthrough conductor passing through the feedthrough substrates 20 and 120, and thus there is no physical pathway between the first surfaces 21 and 121 and the second surfaces 22 and 122 of the feedthrough substrates 20 and 120 that fluid may leak therethrough. Thus, leakage through the feedthrough devices 10 and 110 is simply prevented without the need for complicated and cumbersome processes such as brazing to seal physical passages, and the cause of leakage is fundamentally eliminated, thereby ensuring the prevention of leakage through the feedthrough devices 10 and 110.

The feedthrough devices 10 and 110 according to the embodiments of the present invention shown in FIGS. 3 to 5 may be used in conjunction with housings of devices in which the feedthrough devices 10 and 110 are used, as in the related art of FIG. 1. In this case, the feedthrough substrate is bonded to a housing, where the device is provided, by a brazing process, etc., and the feedthrough substrate may be a ceramic material, but not limited thereto and an insulator is sufficient for the feedthrough substrate. The housing of the device is typically, but not exclusively, made of metal. The present invention is not directed to features associated with the housing, and therefore, the drawings and descriptions thereof are omitted.

Meanwhile, the feedthrough device according to the present invention may be configured to be an integrated body with a liquid crystal polymer (LCP) or polymer material housing of the device having the feedthrough device and made of the same material as the housing of the device. A description will be described in detail with reference to FIGS. 6 to 7.

Figure 6:
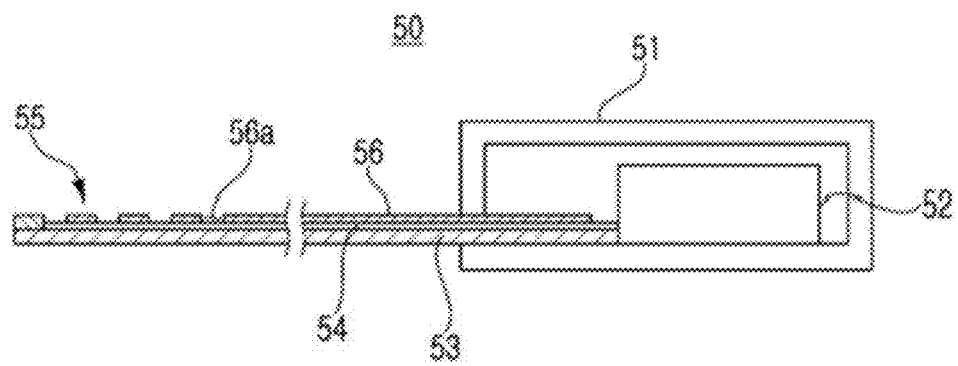
FIG. 6 is a cross-sectional view roughly showing an implantable medical device having a liquid crystal polymer (LCP) or polymer material housing according to the related art.

FIG. 6 is a cross-sectional view roughly showing an implantable medical device having an LCP or polymer material housing according to the related art. Referring to FIG. 6, an implantable medical device 50 having a conventional LCP or polymer material housing (hereinafter referred to as polymer housing) 51 is provided with an electronic circuit board 52 inside the polymer housing 51. A lead wire mounting portion 53 whose one end is coupled to the polymer housing 51 is extended to the outside of the polymer housing 51 and a lead wire 54 connected to the electronic circuit board 52 is provided on the lead wire mounting portion 53. The lead wire mounting portion 53 is provided with an electrode array 55 connected to the lead wire 54 at an opposite end thereof, and a passivation layer 56 covers and protects the lead wire 54 and the electrode array 55. The polymer housing 51, the lead wire mounting portion 53, and the passivation layer 56 are all made of the same or similar thermoplastic materials, and are thermally press bonded to each other by heating with a predetermined temperature and then pressing the above components, thereby enabling to achieve the above-described structure. The conventional method of manufacturing the implantable medical device 50 having the polymer housing 51, including the method of constructing the electronic circuit board 52, the lead wire 54, and the electrode array 55, is well known in the art and will not be described in detail.

The implantable medical device 50 having the conventional polymer housing 51 of the above construction is recognized to be less prone to leakage than an implantable medical device 1 with a conventional metal housing 2 shown in FIG. 1. The main reason is that, unlike FIG. 1 that the metal housing 2 and a ceramic feedthrough substrate 5 made of different materials are bonded by a brazing process, the polymer housing 51, the lead wire mounting portion 53, and the passivation layer 56 made of the same or similar thermoplastic materials are joined together, whereby there is less risk of leakage through the mutually bonded portions. However, even in the case of the implantable medical device 50 having the conventional polymer housing 51, the possibility of leakage due to the body fluid leakage path (extending in parallel with the lead wire) remains, the body fluid leakage path starting from an electrode exposed portion 56a which is formed on the passivation layer 56 to correspond to the electrode array 55, leading to a boundary between the lead wire 54 and the passivation layer 53, and reaching to the electronic circuit board inside the polymer housing 51, but there is no technique to prevent the possibility. However, the present invention suggests a solution to the problem by introducing a feedthrough device.

Figure 7:
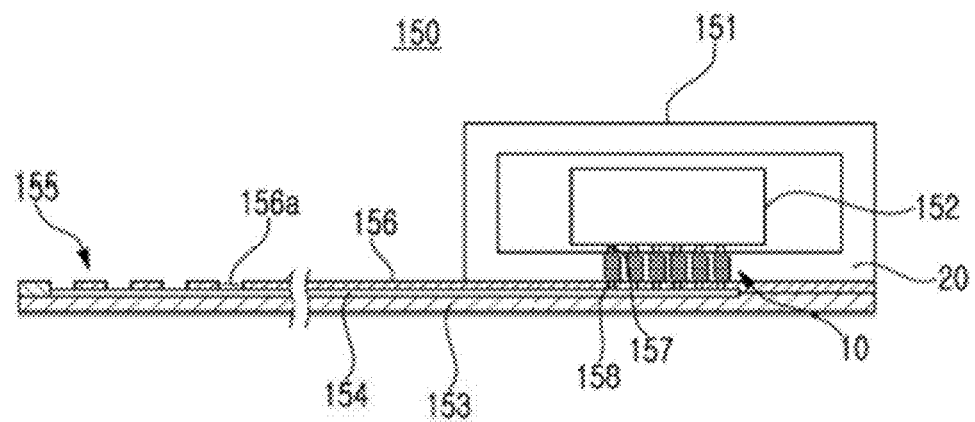
FIG. 7 is a cross-sectional view roughly showing an implantable medical device having an LCP or polymer material housing applied with a feedthrough device according to another embodiment of the present invention.

FIG. 7 is a cross-sectional view roughly showing an implantable medical device having an LCP or polymer material housing (hereinafter referred to as polymer housing, consistent with the description of the related art) applied with a feedthrough device according to another embodiment of the present invention. Referring to FIG. 7, an implantable medical device 150 having a polymer housing 151 according to the present invention is similar to the related art shown in FIG. 6 in that an electronic circuit board 152 is provided inside the polymer housing 151, a lead wire mounting portion 153 whose one end is coupled to the polymer housing 151 is elongated outside the polymer housing 151 and a lead wire 154 connected to the electronic circuit board 152 is mounted on the lead wire mounting portion 153, the lead wire mounting portion 153 is provided with an electrode array 155, which is connected to the lead wire 154, at an opposite end thereof, and a passivation layer 156 covers and protects the lead wire 154 and the electrode array 155, and so on. However, in the present invention, the lead wire 154 on the lead wire mounting portion 153 is not directly connected to the electronic circuit board 152 through the polymer housing 151. The embodiment of the present invention is similar to the feedthrough device 10 described above with reference to FIG. 4 (Elements having similar functions are denoted by the same reference numerals as those in FIG. 4), except that the feedthrough device 10 for electrically connecting the lead wire 154 and the electronic circuit board 152 is provided in the polymer housing 151, the feedthrough substrate 20 of the feedthrough device 10 is made of an LCP or polymer material which is the same material as the polymer housing 151 of the implantable medical device 150 where the feedthrough device 10 is provided and configured to be an integrated body with the polymer housing 151. In FIG. 7, a lower plate of the polymer housing 151 located below the electronic circuit board 152 is the feedthrough substrate 20. Reference numerals 157 and 158 denote electrical connections from the electronic circuit board 152 to the feedthrough device 10 and from the lead wire 154 to the feedthrough device 10, respectively. Reference numeral 156a denotes an electrode exposed portion formed on the passivation layer 156 to correspond to the electrode array 155.

In the implantable medical device 150 having the polymer housing 151 according to the present invention, the lead wire does not penetrate the polymer housing provided with the electronic circuit board such that there is no physical pathway through which fluids including body fluid may leak. Therefore, the cause of leakage is fundamentally eliminated, thereby ensuring the prevention of leakage into the polymer housing.

Although the implantable medical device described so far is provided with the electronic circuit board inside the housing, the implantable medical device in the present invention is not limited thereto and means any device that is implanted in vivo, transmits and receives electrical signals. Thus, implantable stimulators, implantable sensors, implantable cardioverter-defibrillators, neuroprosthetics, neuromodulation devices, as well as implantable connectors are considered to be included in the category for the device.

Figure 8:
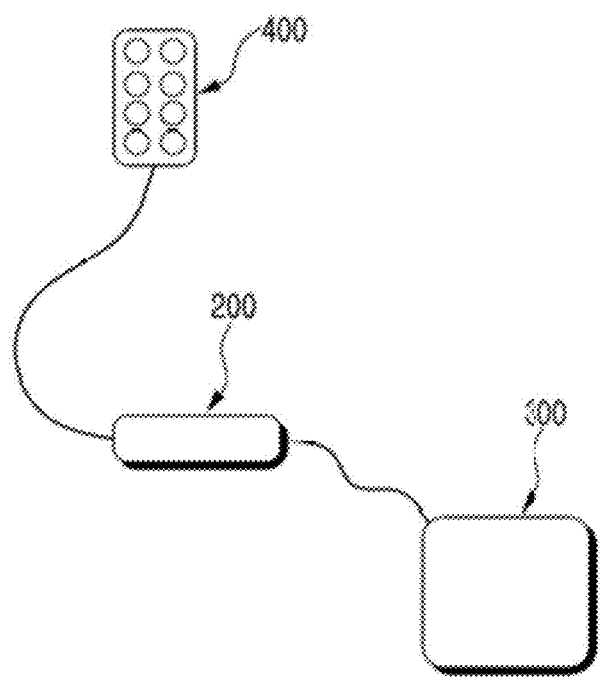
FIG. 8 is a conceptual view showing an example in which an implantable connector is used.

FIG. 8 is a conceptual view showing an example in which an implantable connector is used. Referring to FIG. 8, an implantable connector 200 is disposed between an implantable medical device 300 (neuromodulation device in FIG. 8) and another implantable medical device 400 to connect the implantable medical devices 300 and 400 with each other.

Figure 9:
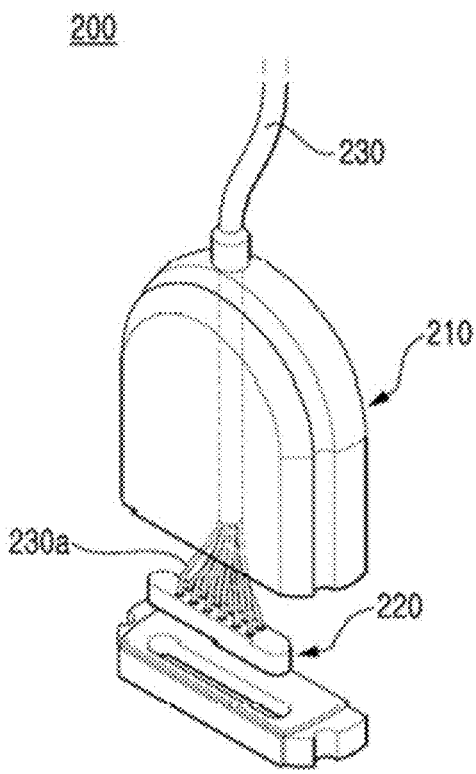
FIG. 9 is an exploded perspective view showing a specific configuration of the implantable connector of FIG. 8.

FIG. 9 is an exploded perspective view showing a specific configuration of the implantable connector of FIG. 8.

Referring to FIG. 9, the implantable connector includes a housing 210 and a feedthrough device 220.

A lead wire 230 extending from another implantable medical device (not shown) penetrates one side of the housing 210 in a sealing manner. That is, the housing 210 is penetrated by the lead wire 230 and a perforated portion thereof is sealed around such that fluids such as body fluid are impossible to leak through the perforated portion. The feedthrough device 220 is provided to electrically connect an end portion 230a of the penetrating and sealed lead wire 230 inside the housing with the outside of the housing 210, in detail, with another implantable medical device outside the housing 210. A detailed configuration of the feedthrough device 220 is the same as that of the feedthrough device of the present invention, and thus a description thereof will be omitted.

In FIG. 9, it is exemplified of the implantable connector 200 in which the lead wire 230 penetrates one side of the housing 210 and is fixed in a sealing manner, but it is also possible to construct an implantable connector in which a housing with both openings surrounds a feedthrough device whose terminals at both surfaces have no connection to a lead wire.

FIGS. 10 to 14 are diagrams showing a method of manufacturing a feedthrough device according to an embodiment of the present invention in order, in particular, a feedthrough device suitable for use in an implantable medical device having a polymer housing.

A molded body is formed for manufacturing a feedthrough device. A molded body 500 is configured with multiple capacitive stacks 510 and a third film 520 interposed between adjacent capacitive stacks 510 (refer to FIG. 10), and those are bonded together (refer to FIG. 11).

Figure 10:
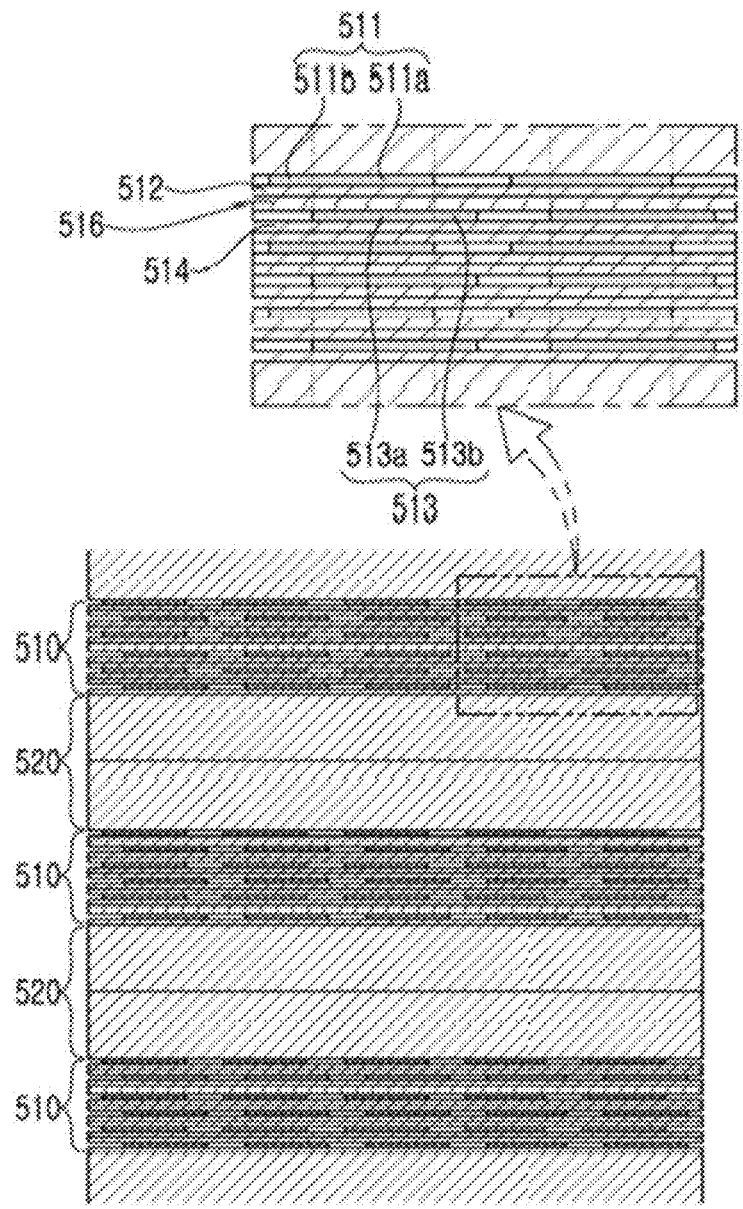
FIGS. 10 to 14 are diagrams showing a method of manufacturing a feedthrough device according to an embodiment of the present invention in order.

As shown in FIG. 10, the capacitive stacks 510 include a structure in which a first film 512 and a second film 514 are alternately stacked, the first film 512 provided with one or more first conductive plates 511 spaced apart from each other and a second film 514 provided with one or more second conductive plates 513 spaced apart from each other. Forming the conductive plates 511 and 513 on the films 512 and 514 may be achieved by any known patterning method.

*As can be understood from the use of the term "include" above, the capacitive stacks 510 may have a layer in addition to the first film 512 and the second film 514.

For example, although not shown in here, the outermost layer of the capacitive stacks 510 may be a layer other than the first film 512 or the second film 514. Also, there may be other layers between the first film 512 and the second film 514. For example, as shown in FIG. 10, a bonding film 516 having a melting point lower than those of the first film 512 and the second film 514 may be further stacked between the first film 512 and the second film 514. Accordingly, it is possible to bond the films 512, 514, and 516 by thermal press bonding, which includes processes of heating at a temperature which is higher than the melting point of the bonding film 516 and lower than the melting point of the first film 512 and the second film 514 and pressurizing.

However, it is understood that it is possible to bond the first film 512 and the second film 514 together without the bonding film 516 by thermal press bonding, which includes processes of heating at a temperature higher than the melting point of the first film 512 and the second film 514, or other known methods.

Figure 11:
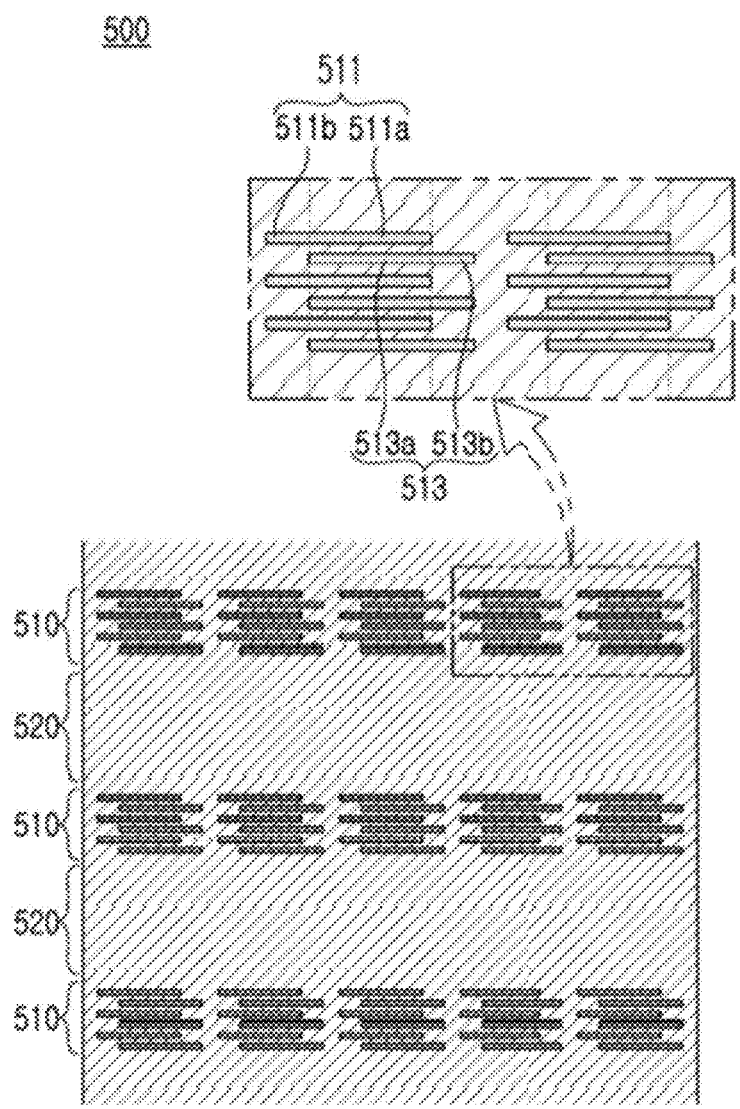

With respect to stacking of the first and second films 512 and 514, the films 512 and 514 are stacked in a manner that the first conductive plate 511 and the second conductive plate 513 are alternated, in order to configure superimposed portions 511a and 513a in which each of the first conductive plate 511 and the second conductive plate 513 superimposes on an orthographic projection of conductive plates, which are adjacent in a vertical direction, in a stacking direction and non-superimposed portions 511b and 513b that do not superimpose on the orthographic projections. In FIGS. 10 and 11, the superimposed portions 511a and 513a are portions inside vertical dotted lines and the non-superimposed portions 511b and 513b are portions outside the vertical dotted lines.

The capacitive stacks 510 are present in plural and the third film 520 is interposed between adjacent capacitive stacks 510. The films 512, 514, and 516 in the capacitive stacks 510 and the third films 520 are bonded together such that the molded body 500 shown in FIG. 11 is obtained. The third film 520 is named differentially by a location thereof, and the thickness of each third film 520 may be different. In addition, since the third film 520 is a name according to a final form after the molded body 500 is obtained, it does not necessarily mean a thick film, but may be multiple thin films that are bonded together and thus have the thickness. Likewise, the third film 520 is not limited to be present in a film state from the outset, that is, present in a solid state, and the present invention includes that the third film 520 is supplied in a fluid state and becomes solidified when the molded body 500 is obtained completely.

As a method for bonding the films 512, 514, 516, and 520 together to obtain the molded body, a thermal press bonding method in which the films are heated at a predetermined temperature and then pressurized is typically, but not necessarily limited thereto. The first film 512, the second film 514, and the third film 520 are made of an LCP or polymer material so as to facilitate bonding by thermal press bonding. In addition, the films can be easily applied to an implantable medical device having a polymer housing, which will be described below with reference to FIG. 15.

As for forming the molded body 500, the embodiment shown in FIGS. 10 and 11 describes the method of forming the molded body by stacking the components of the molded body without bonding, and then boding the components afterward. That is, after the films constituting the molded body are stacked without being bonded together (FIG. 10), the stacked films are bonded together to obtain the molded body (FIG. 11).

However, not shown in here, it is possible to form a molded body by stacking some of the films and then bonding the films together to prepare bonded portions, and then bonding the bonded portions together. For example, after the films 512, 514, and 516 constituting the capacitive stacks 510 are stacked and bonded together to form bonded capacitive stacks, the third film 520 is bonded between the bonded capacitive stacks to obtain the molded body 500. In this case, the third film may be supplied in a fluid state between the bonded capacitive stacks and solidified. For example, for bonding the capacitive stacks, it is possible to apply a double injection molding method in which the bonded capacitive stacks are arranged to be spaced apart from each other with predetermined intervals and a fluid is supplied into the spaces between the capacitive stacks and solidified.

Figure 12:
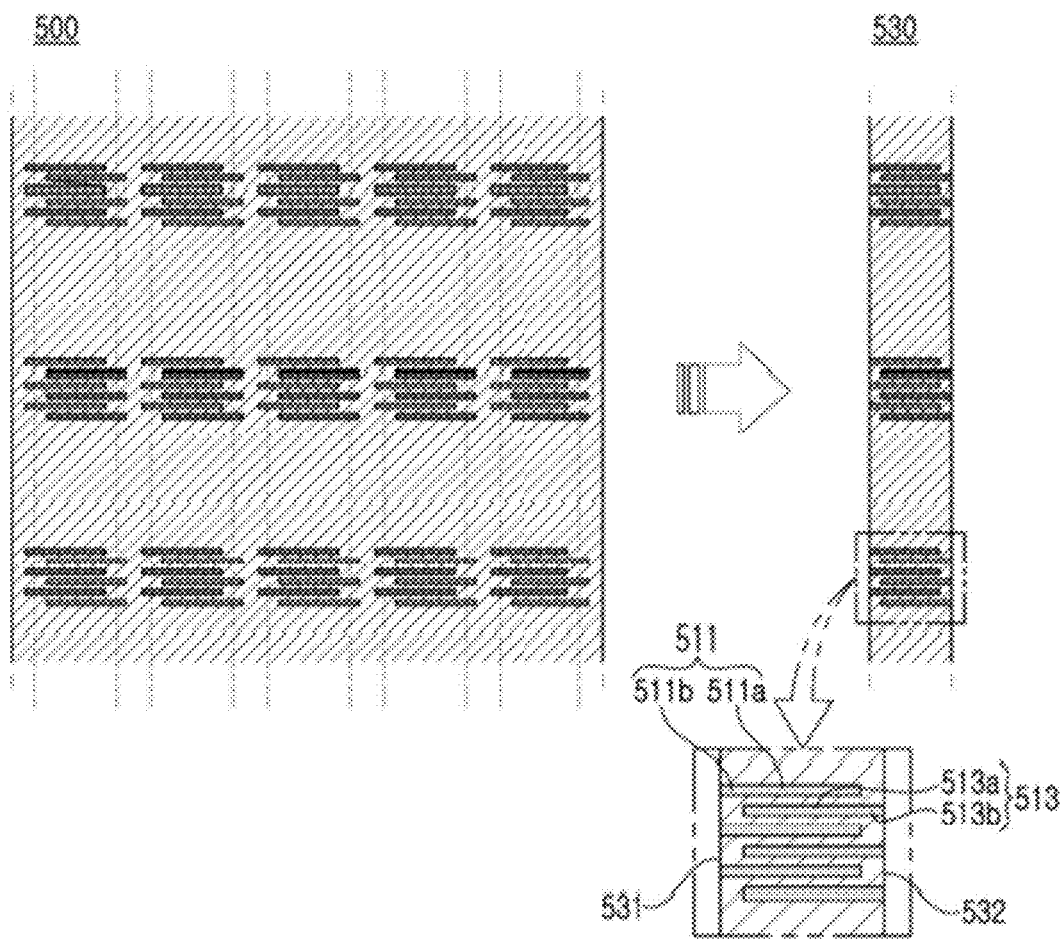

After the molded body 500 is formed by any of those various methods, the molded body 500 is cut along a stacked direction (the cutting line is shown by a dotted line) as shown in FIG. 12 such that at least one cut body 530 is configured in which an end portion of the non-superimposed portion 511b of the first conductive plate 511 is exposed to a first surface 531 and an end portion of the non-superimposed portion 513b of the second conductive plate 513 is exposed to a second surface 532 which is opposite to the first surface 531.

Next, terminals are formed, the terminals connecting the end portions of the non-superimposed portions 511b and 513b exposed to the first surface 531 and the second surface 532 of the cut body 530 with each other respectively.

Figure 13:
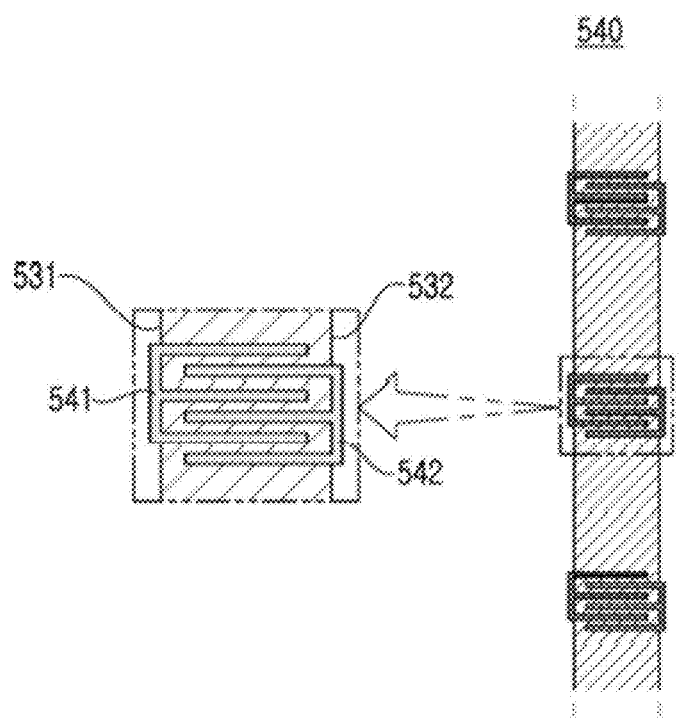

That is, as shown in FIG. 13, multiple first terminals 541 connecting the end portions of the non-superimposed portions 511b of the first conductive plate 511 belonging to each first stacked body (510 of FIG. 10) constituting the cut body 530 are formed on the first surface 531, and multiple second terminals 542 connecting the end portions of the non-superimposed portions 513b of the second conductive plate 513 belonging to each first stacked body are formed on the second surface 532 such that a terminal integration body 540 is configured.

Figure 14:
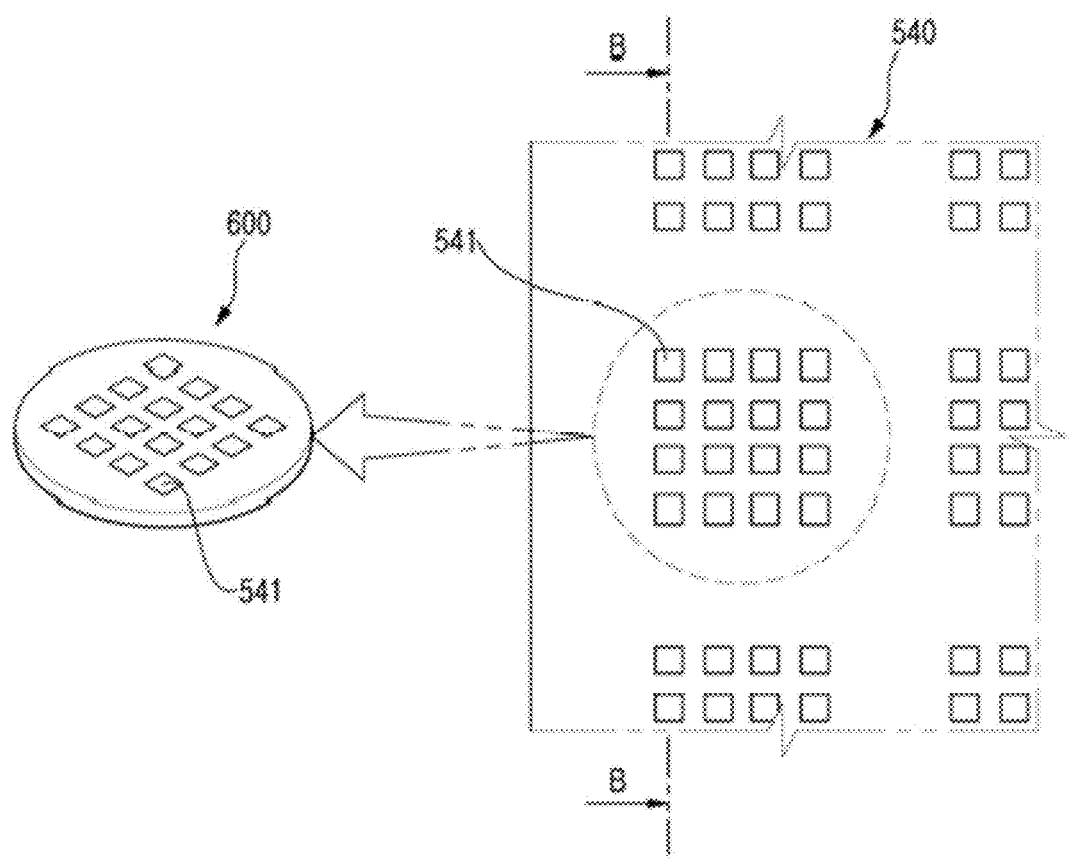

Then, as shown in FIG. 14, the terminal integration body 540 is cut perpendicular to the stacked direction in a manner that the multiple first terminals 541 and the multiple second terminals (not shown in FIG. 14) corresponding thereto are included, such that a feedthrough device 600 is obtained. FIG. 13 shows the stacked direction to be vertical on the drawing sheet, while FIG. 14 shows the stacked direction to be the anterior-posterior direction of the drawing sheet (that is, the direction perpendicular to the surface of the drawing sheet). In other words, a drawing similar to that of FIG. 13 will be obtained by showing a cross section taken along the line B-B in the drawing.

As shown in FIG. 15, which shows the example of using the feedthrough device manufactured by the method shown in FIGS. 10 to 14, when the first terminals 541 on the first surface 531 of the obtained feedthrough device 600 are connected to an electronic circuit board 700, covered with a lid 800, and bonded together, a configuration thereof becomes same with that of FIG. 7 constituting of reference numerals 151, 152, 10, and 20. Accordingly, the feedthrough device may be applied to manufacture an implantable medical device having a polymer housing as shown in FIG. 7.

While the feedthrough device, the method of manufacturing the feedthrough device, and the implantable medical device according to the present invention have been described in connection with the specific embodiments, the embodiments and the drawings are merely illustrative, and the invention is not limited to these embodiments. It is to be understood that various equivalent modifications and variations of the embodiments can be made by a person having an ordinary skill in the art without departing from the spirit and scope of the present invention. Therefore, the true technical scope of the present invention should not be defined by the above-mentioned embodiments but should be defined by the appended claims and equivalents thereof.

INDUSTRIAL APPLICABILITY

The present invention constructed above is applicable to industries related to implantable medical devices such as implantable stimulator, implantable sensor, implantable cardioverter-defibrillator, neuroprosthetics, and neuromodulation device.

The invention claimed is:

1. A feedthrough device configured to be mounted between an interior and an exterior of a housing of an implantable device and transmit an electronic signal to and from an electronic circuit located within the housing, the feedthrough device comprising:

a feedthrough substrate made of an insulator and having a first surface and a second surface;

at least one first feedthrough conductor having a first terminal exposed only to the first surface of the feedthrough substrate and a first body connected to the first terminal and not exposed to the outside of the feedthrough substrate; and at least one second feedthrough conductor having a second terminal exposed only to the second surface of the feedthrough substrate and a second body connected to the second terminal and not exposed to the outside of the feedthrough substrate, and corresponding to the first feedthrough conductor in a one-to-one manner to be paired therewith;

wherein the first body of each first feedthrough conductor and the second body of each second feedthrough conductor corresponding thereto are arranged to be capacitively coupled with each other;

wherein the feedthrough device is configured so that one of the first surface and the second surface is inside the housing toward the electronic circuit and another one of the first surface and the second surface is outside of the housing away from the electronic circuit; and wherein transmission of an electronic signal to and from the electronic circuit is by way of capacitive coupling between the at least one first feedthrough conductor and the at least one second feedthrough conductor.

2. The feedthrough device of claim 1, wherein the first body of each first feedthrough conductor is provided with at least one first branch and the second body of each second feedthrough conductor corresponding thereto is provided with at least one second branch such that the first feedthrough conductor and the corresponding second feedthrough conductor are disposed such that the branches are arranged in an alternate manner.

3. The feedthrough device of claim 2, wherein the first branch of the first feedthrough conductor and the second branch of the corresponding second feedthrough conductor, which are arranged alternately, are substantially parallel.

4. The feedthrough device of claim 2, wherein the first surface and the second surface of the feedthrough substrate are substantially parallel, and the first branch of the first feedthrough conductor and the second branch of the second feedthrough conductor are substantially parallel to the first surface and the second surface of the feedthrough substrate.

5. The feedthrough device of claim 2, wherein the first surface and the second surface of the feedthrough substrate are substantially parallel, and the first branch of the first feedthrough conductor and the second branch of the second feedthrough conductor are substantially perpendicular to the first surface and the second surface of the feedthrough substrate.

6. The feedthrough device of claim 1, wherein the first body of the first feedthrough conductor is one of a plurality of first bodies disposed to be spaced apart from each other at first equal intervals, and the second body of the second feedthrough conductor is one of a plurality of second bodies disposed to be spaced apart from each other at second equal intervals.

7. The feedthrough device of claim 1, wherein the feedthrough substrate is bonded to a housing where the feedthrough device is provided, and made of a ceramic material.

8. The feedthrough device of claim 1, wherein the feedthrough substrate is configured to be an integrated body with a liquid crystal polymer (LCP) or polymer material housing of the implantable device which houses the feedthrough device, the feedthrough substrate being made of the same material as the housing.

9. An implantable medical device comprising:
a housing, an electronic circuit located in the housing, and a feedthrough device provided between an interior and an exterior of inside the housing and used to transmit an electronic signal to and from the electronic circuit, wherein the feedthrough device includes:
a feedthrough substrate made of an insulator and having a first surface and a second surface;
at least one first feedthrough conductor having a first terminal exposed only to the first surface of the feedthrough substrate and a first body connected to the first terminal and not exposed to the outside of the feedthrough substrate; and
at least one second feedthrough conductor having a second terminal exposed only to the second surface of the feedthrough substrate and a second body connected to the second terminal and not exposed to the outside of the feedthrough substrate, and corresponding to the first feedthrough conductor in a one-to-one manner to be paired therewith,
wherein the first body of each first feedthrough conductor and the second body of each second feedthrough conductor corresponding thereto are arranged to be capacitively coupled with each other;
wherein the feedthrough device is configured so that one of the first surface and the second surface is inside the housing toward the electronic circuit and another one of the first surface and the second surface is outside of the housing away from the electronic circuit; and
wherein transmission of an electronic signal to and from the electronic circuit is by way of capacitive coupling between the at least one first feedthrough conductor and the at least one second feedthrough conductor.

10. The implantable medical device of claim 9, wherein the first body of each first feedthrough conductor is provided with at least one first branch and the second body of each second feedthrough conductor corresponding thereto is provided with at least one second branch such that the first feedthrough conductor and the corresponding second feedthrough conductor are disposed such that the branches are arranged in an alternate manner.

11. The implantable medical device of claim 10, wherein the first branch of the first feedthrough conductor and the second branch of the corresponding second feedthrough conductor, which are arranged alternately, are substantially parallel.

12. The implantable medical device of claim 10, wherein the first surface and the second surface of the feedthrough substrate are substantially parallel, and the first branch of the first feedthrough conductor and the second branch of the second feedthrough conductor are substantially parallel to the first surface and the second surface of the feedthrough substrate.

13. The implantable medical device of claim 10, wherein the first surface and the second surface of the feedthrough substrate are substantially parallel, and the first branch of the first feedthrough conductor and the second branch of the second feedthrough conductor are substantially perpendicular to the first surface and the second surface of the feedthrough substrate.

14. The implantable medical device of claim 9, wherein the first body bodies of the first feedthrough conductor is one of a plurality of first bodies disposed to be spaced apart from each other at first equal intervals, and the second body of the second feedthrough conductor is one of a plurality of second bodies disposed to be spaced apart from each other at second equal intervals.

* * * * *